United States Patent [19]
Wright

[11] Patent Number: 5,522,884
[45] Date of Patent: Jun. 4, 1996

[54] HOLDER FOR ADJUSTABLE MITRAL & TRICUSPID ANNULOPLASTY RINGS

[75] Inventor: John T. M. Wright, Conifer, Colo.

[73] Assignee: Medtronic, Inc., Minneapolis, Minn.

[21] Appl. No.: 19,515

[22] Filed: Feb. 19, 1993

[51] Int. Cl.⁶ ..................................................... A61F 2/24
[52] U.S. Cl. ................................................. 623/2; 606/148
[58] Field of Search ........................ 623/2, 900; 606/148, 606/232

[56] References Cited

U.S. PATENT DOCUMENTS

| | | | |
|---|---|---|---|
| 3,828,787 | 8/1974 | Anderson et al. | 606/1 |
| 4,042,979 | 8/1977 | Angell | 623/2 |
| 4,702,250 | 10/1987 | Ovil et al. | 606/148 |
| 5,041,130 | 8/1991 | Cosgrove et al. | 623/2 |

FOREIGN PATENT DOCUMENTS

1008937  7/1984  U.S.S.R. ................................. 623/2

*Primary Examiner*—David H. Willse
*Attorney, Agent, or Firm*—Reed A. Duthler; Harold R. Patton

[57] ABSTRACT

A holder that aids the implantation of adjustable annuloplasty rings. The holder has an annular recess around its periphery, into which the inner portion annuloplasty ring containing the drawstring is retained, thus protecting the drawstrings from the implanting suture needle. The holder is also provided with one or more suture snuggers for tensioning the drawstring.

14 Claims, 7 Drawing Sheets

HOLDER FOR ADJUSTABLE MITRAL & TRICUSPID ANNULOPLASTY RINGS

BACKGROUND OF THE INVENTION

The present invention relates to surgical tools generally and more specifically to tools for use when implanting annuloplasty rings for the surgical correction of certain mitral or tricuspid valve disorders.

Adjustable annuloplasty rings contain internal drawstrings that allow the diameter of the ring to be reduced following the suturing of the ring into the annulus, to minimize any residual regurgitation. When suturing such rings in place it is important that the implanting sutures do not interfere with the function of the internal drawstrings that allow the circumference of the ring to be reduced. A holder for a non-adjustable annuloplasty ring was described in U.S. Pat. No. 5,011,481. This device, for use with the Duran annuloplasty ring, uses a plurality of fingers extending from an outer circumferential surface. An alternative annuloplasty ring holder for use with the Duran ring is also described in the brochure entitled "Conservative repair of Mitral and Tricuspid Valves" by Garcia-Rinaldi et al. An additional annuloplasty ring holder for use with a fixed circumference annuloplasty ring is described in U.S. Pat. No. 5,041,130, issued to Cosgrove et al.

An annuloplasty ring holder is provided by St. Jude Medical with its "BiFlex" adjustable annuloplasty ring, as described in brochures distributed with the rings. This holder employs radially extending projections which engage the upper and lower surfaces of the ring and serve as suturing templates. This holder does not protect the drawstrings during suture placement, nor provide means for trial adjustments to be made to the drawstrings.

SUMMARY OF THE INVENTION

It is an objective of this invention to provide a simple, disposable surgical tool for holding a flexible, adjustable annuloplasty ring for use in tricuspid and mitral valve repair.

It is a further objective of this invention to provide an annuloplasty ring holder that will prevent the needles of the implantation sutures from interfering with the adjusting drawstrings of said annuloplasty ring.

It is a further objective of this invention to provide an annuloplasty ring holder that will allow the adjustable annuloplasty ring to have a preliminary adjustment made (by means of its internal drawstrings) and the valve tested for regurgitation prior to the tying of the drawstrings.

In the embodiment of the present invention intended for use in conjunction with a mitral annuloplasty ring, it is a further objective to retain the ring in an anatomically correct three dimensional configuration during placement of the sutures holding the ring to the valve annulus.

The preferred embodiment of the invention comprises an annular member and a stem and handle member and incorporates one or two detachable suture snuggers. The snuggers allow the ring to be adjusted and the valve tested for reflux prior to tying the annuloplasty ring drawstring, and also assist in keeping the drawstrings organized and tangle-free during suturing of the annuloplasty ring to the valve annulus. The annular member has a recess around its periphery into which the portion of the annuloplasty ring containing the drawstrings is inserted. The drawstrings of the annuloplasty ring are typically located adjacent the interior of the ring, and the recess thus serves to protect the drawstrings from

2 damage due to passage of needles through the ring. In the preferred embodiment of the holder for use in conjunction with a mitral annuloplasty ring, the annular member has an angled flat face to retain the anterior portion of the ring at an appropriate angle to the plane generally defined by the remainder of the ring.

The holder is particularly intended for use with the annuloplasty rings described in allowed U.S. Pat. No. 5,201,880, issued to Wright et al. for Mitral and Tricuspid Annuloplasty Rings, incorporated herein by reference in its entirety. However, the holder may also be used in combination with other adjustable annuloplasty rings.

Other objectives and advantages of this invention will be more apparent from the detailed description of the device which follows.

BRIEF DESCRIPTION OF THE DRAWINGS

The present invention may be better understood and the advantages will become apparent to those skilled in the art by reference to the accompanying drawings, wherein like reference numerals refer to like elements in the several figures, and wherein.

DETAILED DESCRIPTION OF THE PREFERRED EMBODIMENTS

Figure 1:
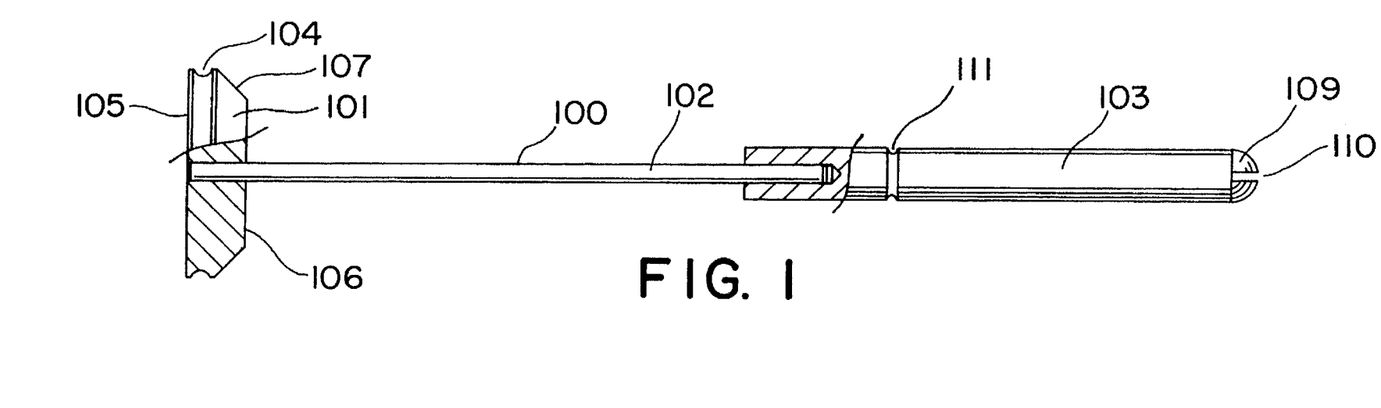
FIG. 1 shows a part cutaway side view of the holder.
Figure 2:
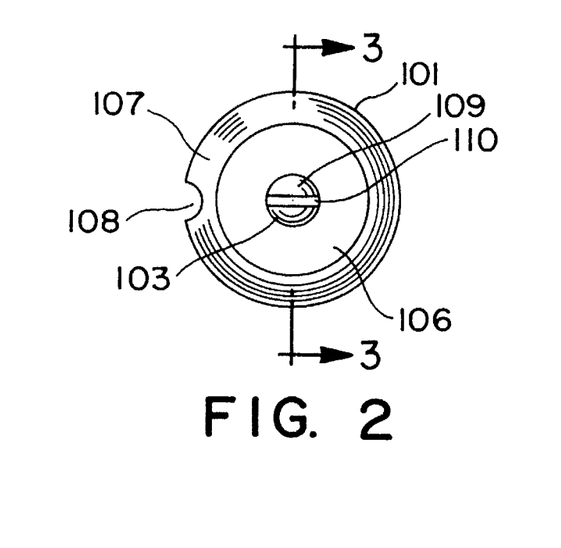
FIG. 2 shows an end view of the holder shown in FIG. 1.

FIG. 1 is a part sectional side view taken along line AA of FIG. 2, and FIG. 2 shows an end view of the holder 100, comprising of holder member 101, malleable stem 102 and handle member 103. Holder member 101, which may conveniently made from a biocompatible thermoplastic such as polysulfone, has an annular, circumferential recess 104. Holder 101 may be fixed to malleable stem 102 using an interference fit, a suitable adhesive or using an insert molding technique. The malleable stem 102 may be an anodized aluminum alloy, and may be affixed to handle member 103 by an interference fit, an adhesive or other suitable means. Handle member 103 may be of metal, such as an anodized aluminum alloy, or a suitable plastic material. The outer surface may be knurled to provide a non-slip finish. Holder 101 has faces 105 and 106, a conical portion 107, and a slot or recess 108. Handle 103 is terminated in a hemispherical surface 109, containing a radial slot 110, and also has an annular groove 111 located at a suitable distance from the junction of stem 102 and handle 103.

Figure 3:
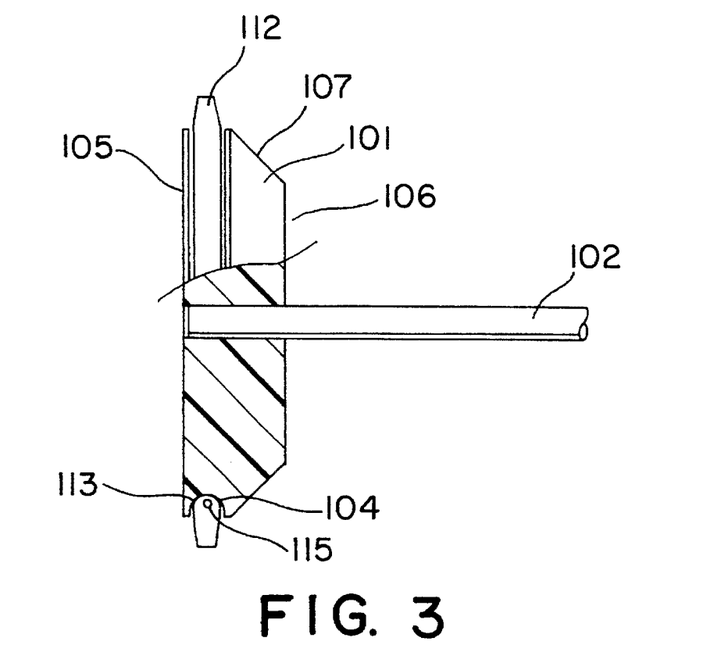
FIG. 3 shows a part cross-section of an annuloplasty ring retained in the holder.

FIG. 3 shows a part cross sectional side view of the holder 101, with an adjustable annuloplasty ring 112 in situ. The inner face of the annuloplasty ring 113 is located in annular recess 104, and held in situ by an internal drawstring 115, tensioned as described below to hold the ring within recess 104.

Figure 4:
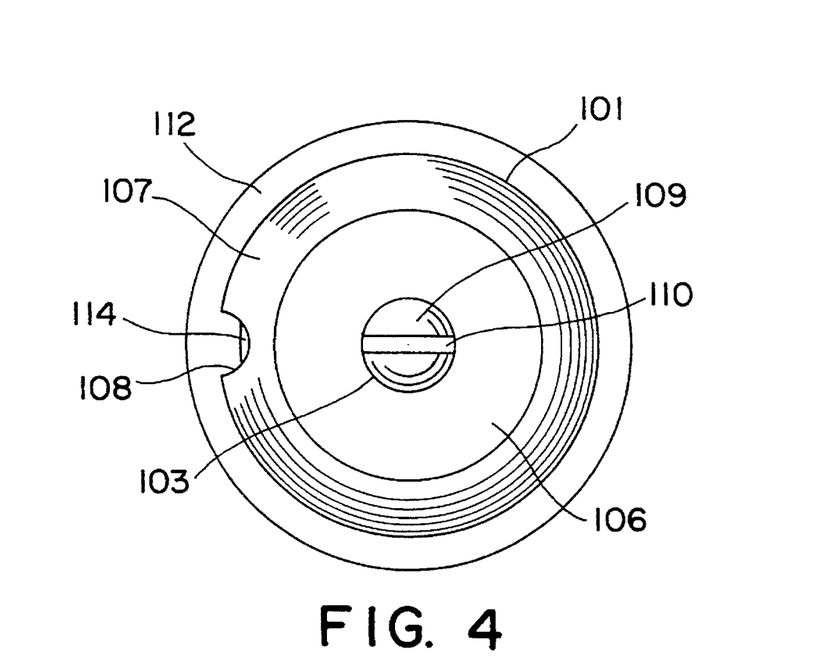
FIG. 4 shows an end view of the holder with an annuloplasty ring in situ.

FIG. 4 shows an end view of the holder with an annuloplasty ring in situ. An opening 114 is defined by recess 108 and the inner face 113 of the annuloplasty ring 112. Opening 114 is provided so that one tip of a pair of forceps may be inserted to assist in removing the annuloplasty ring 112 from the holder 101.

Figure 5:
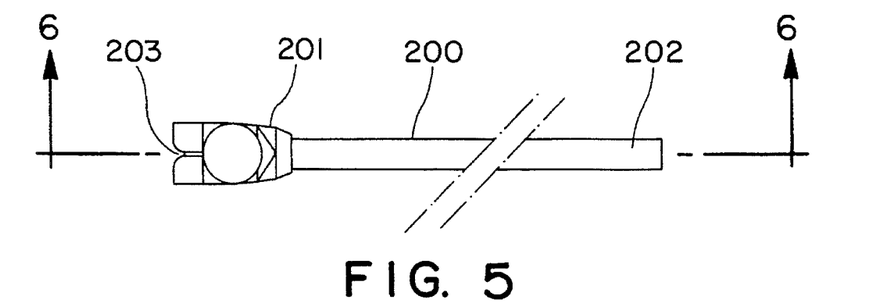
FIG. 5 shows a plan view of a commercially available snugger.
Figure 6:
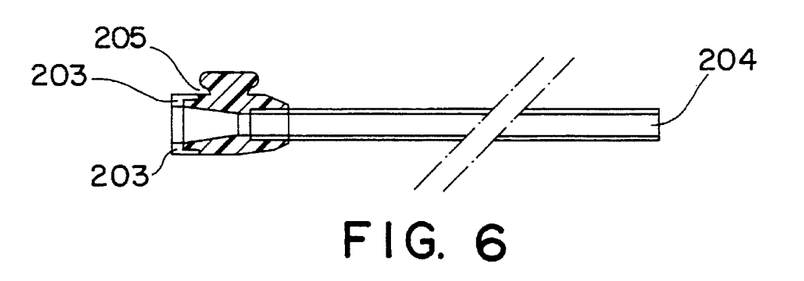
FIG. 6 shows a cross sectional view of a commercially available snugger.
Figure 7:
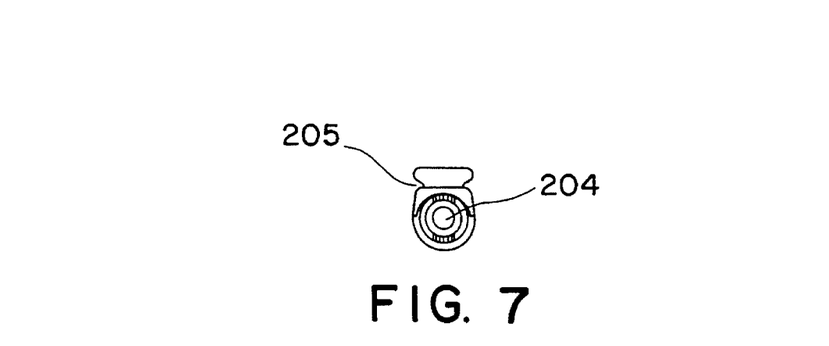
FIG. 7 shows an end view of a commercially available snugger.

FIG. 5 shows a plan view, FIG. 6 shows a cross sectional view taken along line BB of FIG. 5, and FIG. 7 shows an end view of a commercially available snugger of the type manufactured by DLP, Inc. It consists of a body 201, a flexible tube 202 with lumen 204. Body 201 has a pair of slots 203 and an annular recess 205. This device is used as a snugger in cardiovascular surgery. In such use, one or usually two ligatures are passed along the length of tube 202, are tightened, passed into a slot 203, and wound around recess 205 to anchor the sutures in place relative to the snugger.

Figure 8:
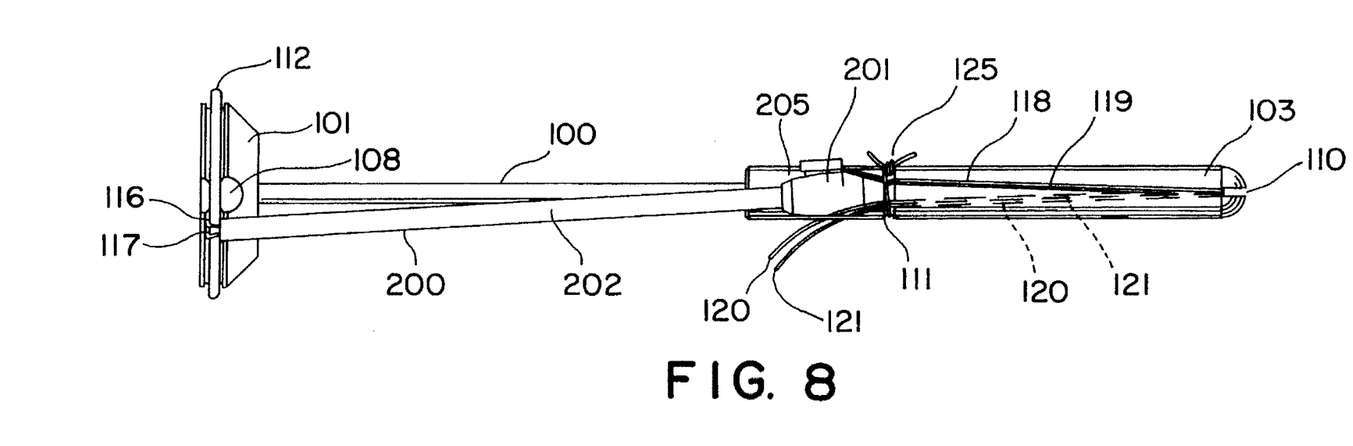
FIG. 8 shows a side view of the holder and snugger with an annuloplasty ring in situ.
Figure 9:
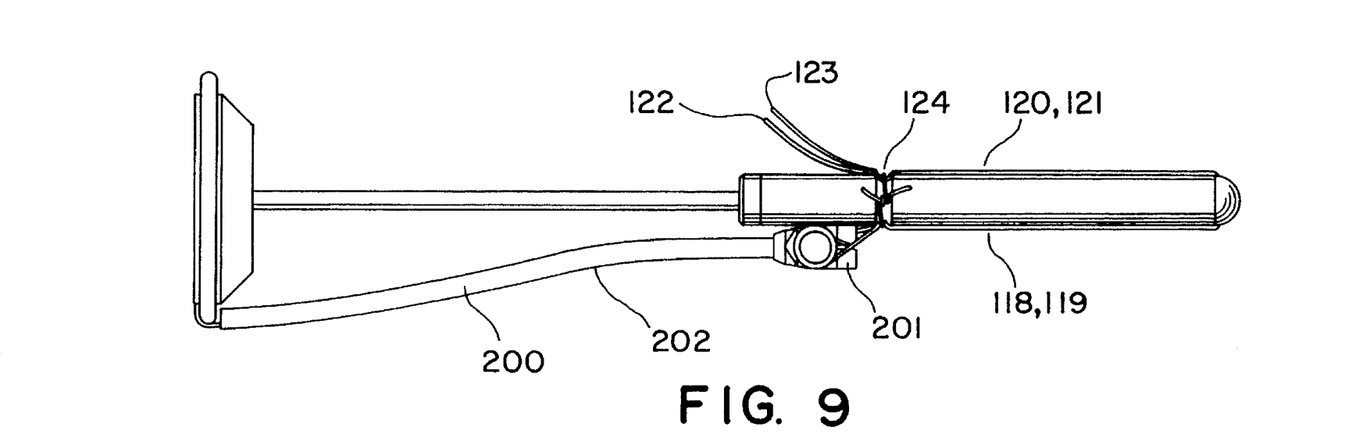
FIG. 9 shows a plan view of the holder and snugger with an annuloplasty ring in situ.

FIG. 8 shows a side view and FIG. 9 shows a plan view of the holder and snugger with an annuloplasty ring in situ. Annuloplasty ring 112 has a single pair of drawstrings 116, 117 that pass into flexible tube 202 of snugger 200. The drawstrings emerge from snugger body 201, pass through slot 203 (FIG. 5) and are wound around slot 205 (FIG. 5) to maintain tension on the drawstrings and thereby retain the ring 112 on holder 101. The drawstrings then pass along the length of the handle 103 at 118 and 119, pass through slot 110 and return along the opposite side of handle 103 at 120 and 121. The drawstrings 116, 117 are retained in position by means of a tie 124 contained in annular grove 111. This tie also serves to retain snugger 200 in position. Tie 124 is retained in slot 111 by means of a knot 125. Drawstrings 116 and 117 terminate at 122 and 123 respectively.

Figure 10:
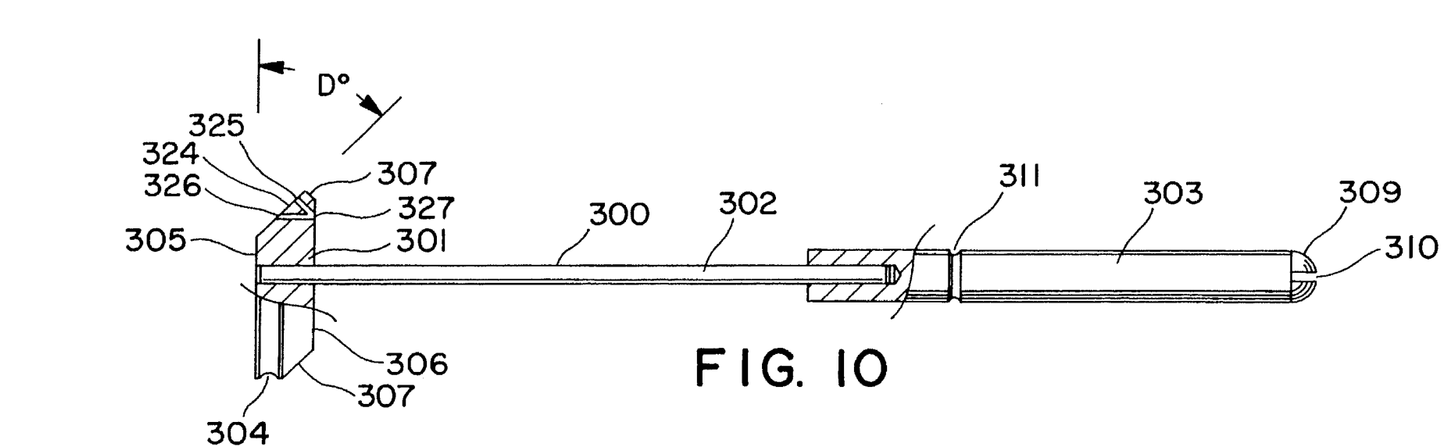
FIG. 10 shows a part sectional side view of the preferred embodiment of the ring intended for use with a mitral annuloplasty ring.
Figure 11:
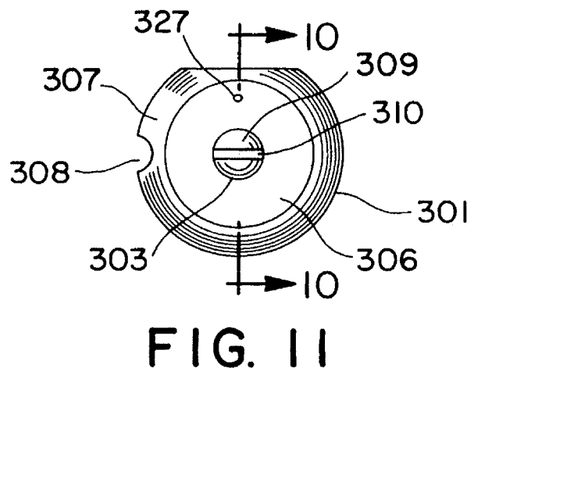
FIG. 11 shows a end view of the preferred embodiment of the holder intended for use with a mitral annuloplasty ring.
Figure 12:
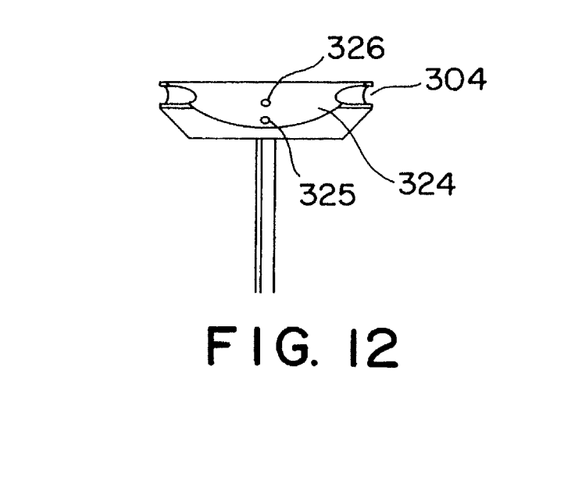
FIG. 12 shows a part plan view of the preferred embodiment of the holder intended for use with a mitral annuloplasty ring.

FIG. 10 shows a part sectional side view of the holder intended for annuloplasty rings used in mitral valve repair, taken along line CC of FIG. 11. An end view is shown in FIG. 11, and FIG. 12 shows a part plan view of the same apparatus. The holder 300, comprising of holder member 301, malleable stem 302 and handle member 303. Holder member 301, which may conveniently made from a biocompatible thermoplastic such as polysulfone, has an annular recess 304. Holder 301 may be fixed to malleable stem 302 using an interference fit, a suitable adhesive or using an insert molding technique. The malleable stem 302 may be an anodized aluminum alloy, and may be affixed to handle member 303 by an interference fit, an adhesive or other suitable means. Handle member 303 may be of metal, such as an anodized aluminum alloy, or a suitable plastic material. The outer surface may be knurled to provide a non-slip finish. Holder 301 has faces 305 and 306, a conical portion 307, and an annular slot 308. Recess 308 provides space so that one tip of a pair of forceps may be inserted to assist in removing the mitral annuloplasty ring from the holder 301. Handle 303 is terminated in a hemisphere 309, containing a radial slot 310, and also has an annular groove 311 located at a suitable distance from the junction of stem 302 and handle 303. Holder member 301 has a flat face 324 inclined at an angle D° to face 305. Angle D° may range from about 25° to 75° and may conveniently be 45° as shown. Face 324 is provided with two holes 325 and 326, each of approximately 0.030" diameter. Hole 325 is normal to face 324, while hole 326 is normal to face 306. Holes 325 and 326 intersect to form a common cavity 327.

Figure 13:
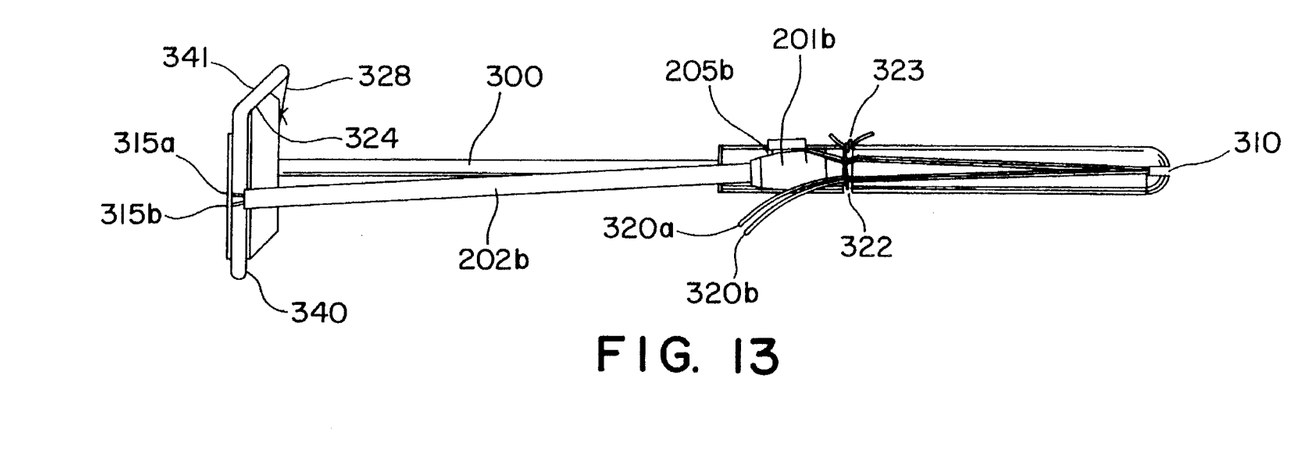
FIG. 13 shows a side view of the preferred embodiment of the holder and snugger for use with a mitral annuloplasty ring, with a mitral annuloplasty ring in situ.
Figure 14:
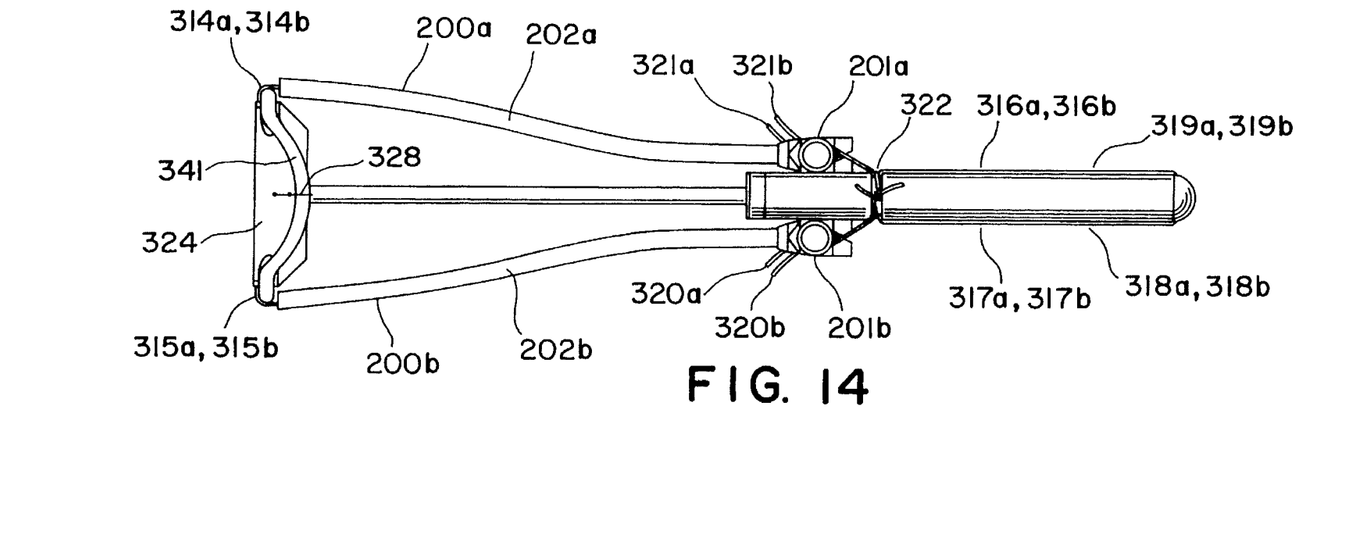
FIG. 14 shows a plan view of the preferred embodiment of the holder and snugger for use with a mitral annuloplasty ring, with a mitral annuloplasty ring in situ.

FIG. 13 shows a side view of the preferred embodiment of the holder illustrated in FIGS. 10–12, with snuggers and a mitral annuloplasty ring in situ. FIG. 14 shows a plan view of the preferred embodiment of the holder and snuggers, with a mitral annuloplasty ring in situ. Annuloplasty ring 340 has a two pair of drawstrings 314a, 314b and 315a, 315b that pass into flexible tubes 202a, 202b of snuggers 200a, 200b. The drawstrings emerge from snugger bodies 201a, 201b to pass along slots 203 (FIG. 5.) and pass in recesses 205a, 205b of snuggers 200a, 200b respectively, to maintain tension on the internal drawstrings within ring 341 and thereby retain it in recess 304 (FIG. 11). The drawstrings 314a, 314b then pass along the length of the handle 303 at 316a, 316b, pass through slot 310 and hence return along the opposite side of handle 303 at 318a, 318b to terminate at 320a, 320b. Likewise, the drawstrings 315a, 315b pass along the length of the handle 303 at 317a, 317b, pass through slot 310 and hence return along the opposite side of handle 303 at 319a, 319b to terminate at 321a, 321b respectively. The drawstrings 314a, 314b, 315a, 315b are retained in position by means of a tie 322 contained by annular grove 311. This tie also retains snuggers 200a, 200b in position. Tie 322 is retained in slot 311 by means of a knot 323. The anterior segment 341 of the mitral annuloplasty ring 340 is retained against face 324 by means of suture 328, whereby it is appropriately three dimensionally configured for attachment to the mitral valve annulus.

Figure 15:
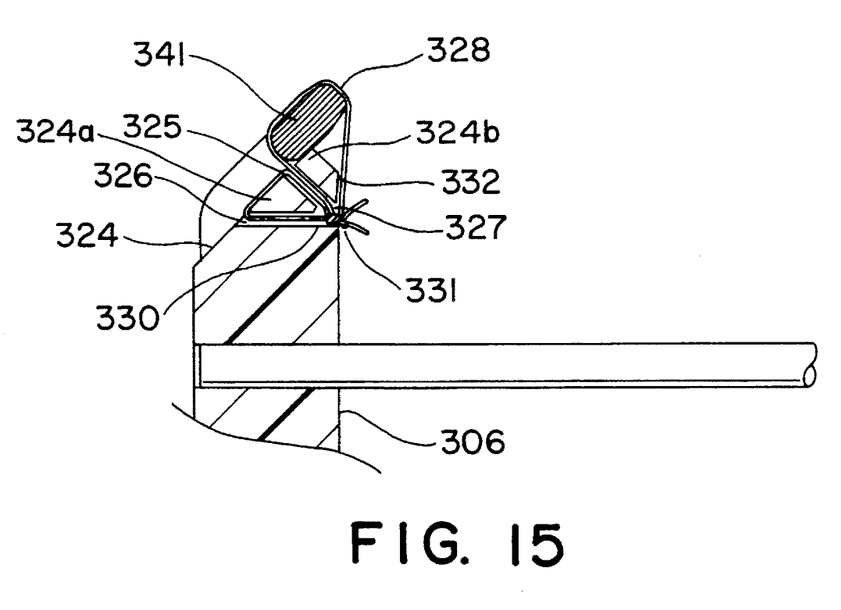
FIG. 15 shows a part cross-sectional view taken along line CC of FIG. 11 with a mitral annuloplasty ring retained.

FIG. 15 shows a part cross-sectional view taken along line CC of FIG. 11 with the anterior segment 341 of the mitral annuloplasty ring retained and inclined along face 324 by suture 328. Suture 328 may conveniently be composed of a size b 4.0green braided polyester surgical suture material. In assembly, the mitral annuloplasty ring is placed on holder member 306 and a suitable length of suture material is passed through hole 326 from 306 to emerge at face 324. The end of the suture is then passed through hole 325 to emerge at face 306. Knot 330 is then tied and pulled into cavity 327. One free end of knot 330 is then passed along hole 325 to emerge at face 324. This free end is then passed around anterior segment 341 of the mitral annuloplasty ring 340 and tied to the other free end of first knot 330 to form second knot 331. First knot 330 lies in cavity 327. In use when the surgeon wishes to free the anterior segment 341 of the mitral annuloplasty ring 340 from the holder, suture 328 is cut in the vicinity of portion 332 thus freeing anterior portion 341 of said annuloplasty ring 340 from said holder 306, the suture is prevented from falling from holder by knot 330. Application of atraumatic forceps in annular recess 308 (FIG. 11) aids the removal of mitral annuloplasty ring 340 from holder member 306.

In use the annuloplasty ring and snuggers are mounted onto the holder at time of manufacture, and the assembly is provided as a sterile unit. The surgeon bends the malleable handle to a convenient angle, depending upon the particular anatomical exposure of the tricuspid or mitral valve being repaired. The implanting sutures are placed in the annulus and through the sewing potion of the ring. Using the handle, the ring is pushed down the suture bundle so that the ring lies close to the tissue annulus. The suture tie on the handle is cut, releasing the drawstrings and snugger. One tip of a pair of atraumatic forceps is then pushed into the slot between the ring and the holder, and the ring gently removed from the holder which is then discarded. The implanting sutures are then tied, and the competency of the valve tested. If required, one or more drawstrings are tightened using the snugger to minimize regurgitation, and valve competency reassessed. When an acceptable result is obtained, the snugger is removed and discarded, and the drawstrings tied.

In conjunction with the above specification, I claim:

I claim:

1. A holder and an annuloplasty ring in combination, comprising:

an annuloplasty ring having a ring body including an internal drawstring extending over a portion of the circumference of said ring body and located adjacent an inner surface of said ring body;

a holder member having an outer circumferential surface to which said annuloplasty ring is mounted, said member having an annular recess into which said portion of said circumference of said annuloplasty ring containing said drawstring is inserted such that said drawstring lies within said annular recess.

2. A holder and annuloplasty ring according to claim 1 wherein a portion of said internal drawstring extends exterior to said annuloplasty ring body, further comprising snugger means for applying and maintaining tension on said drawstring.

3. A holder and annuloplasty ring according to claim 2 wherein said snugger means comprises means for applying and maintaining tension on said drawstring, while said annuloplasty ring is mounted to said holder member.

4. A holder and annuloplasty ring according to claim 2 wherein said snugger means comprises means for applying and maintaining tension on said drawstring, while said annuloplasty ring is dismounted from said holder member.

5. A holder and annuloplasty ring according to claim 2 wherein said snugger is removably mounted to said holder.

6. A holder and annuloplasty ring according to claim 5 wherein said portion of said drawstring extending exterior to said annuloplasty ring body is employed to removably mount said snugger means to said holder.

7. A holder and annuloplasty ring according to claim 6 wherein said holder further comprises a handle member extending from said holder member and having an annular groove, around which said drawstring is wrapped to retain said snugger means.

8. A holder and annuloplasty ring according to claim 1 wherein said holder member is provided with a recess located extending inward of said annular groove such that an opening is defined between said ring and said holder member.

9. A holder and an annuloplasty ring in combination, comprising:

an annuloplasty ring having a ring body including an internal drawstring extending over a portion of the circumference of said ring body;

a holder member having an outer circumferential surface to which said annuloplasty ring is mounted, and snugger means for tensioning said drawstring to retain said annuloplasty ring on said holder member.

10. A holder and annuloplasty ring according to claim 9 wherein said snugger means comprises means for applying and maintaining tension on said drawstring, while said annuloplasty ring is mounted to said holder member.

11. A holder and annuloplasty ring according to claim 9 wherein said snugger means comprises means for applying and maintaining tension on said drawstring, while said annuloplasty ring is dismounted from said holder member.

12. A holder and annuloplasty ring according to claim 9 wherein said snugger is removably mounted to said holder.

13. A method of implanting an adjustable annuloplasty ring of the type employing a drawstring, comprising:

mounting said ring to a holder;

passing said drawstring through a suture snugger and mounting said snugger to said holder;

suturing said ring to a heart valve annulus;

removing said ring and said suture snugger from said holder;

employing said suture snugger to temporarily adjust the configuration of said ring by temporarily securing said drawstring; and permanently securing said drawstring.

14. A method according to claim 13 further comprising the step of employing said drawstring to removably secure said suture snugger to said holder.

* * * * *